US010809266B2

(12) United States Patent
Peikon et al.

(10) Patent No.: US 10,809,266 B2
(45) Date of Patent: Oct. 20, 2020

(54) QUANTITATIVE MASSIVELY PARALLEL PROTEOMICS

(71) Applicant: Verily Life Sciences LLC, Mountain View, CA (US)

(72) Inventors: Ian Peikon, Bethpage, NY (US); Gary Tong, Berkeley, CA (US); Daniel Liu, Berkeley, CA (US); Ci Chu, Palo Alto, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 256 days.

(21) Appl. No.: 15/656,423

(22) Filed: Jul. 21, 2017

(65) Prior Publication Data

US 2018/0024139 A1 Jan. 25, 2018

Related U.S. Application Data

(60) Provisional application No. 62/365,542, filed on Jul. 22, 2016.

(51) Int. Cl.
*G01N 33/68* (2006.01)
*G01N 33/58* (2006.01)
*C12Q 1/6804* (2018.01)

(52) U.S. Cl.
CPC ....... *G01N 33/6845* (2013.01); *C12Q 1/6804* (2013.01); *G01N 33/58* (2013.01); *G01N 2458/10* (2013.01); *G01N 2570/00* (2013.01)

(58) Field of Classification Search
None
See application file for complete search history.

(56) References Cited

U.S. PATENT DOCUMENTS

| 2007/0003950 | A1  | 1/2007  | Shen et al. |
| 2014/0256588 | A1* | 9/2014  | Glezer ............. G01N 33/54353 506/9 |
| 2015/0376609 | A1  | 12/2015 | Hindson et al. |
| 2019/0025299 | A1* | 1/2019  | Vigneault .......... C07K 14/7051 |

FOREIGN PATENT DOCUMENTS

WO 2016100976 6/2016

OTHER PUBLICATIONS

Alves et al. (Bioconjugate Chem 2014 25: 1198-1202) (Year: 2014).*
BD Biosciences, Intracellular FLow Cytometry, 2012.
Fluidigm, Helios, a CyTOF System, 2015, https://www.fluidigm.com/products/helios#overview.
Ahram et al., "Estimation of membrane proteins in the human proteome", In silico biology 6.5 (2006): 379-386.

(Continued)

*Primary Examiner* — Changhwa J Cheu
(74) *Attorney, Agent, or Firm* — Kilpatrick Townsend & Stockton LLP

(57) ABSTRACT

Provided herein are compositions and methods for the identification of an expression profile in a single cell or population of cells. Kits for use with the disclosed methods are also provided, including antibodies, with a unique molecular identifier and antibody identifier, and primers for amplification of the antibody identifier sequence.

20 Claims, 7 Drawing Sheets

Specification includes a Sequence Listing.

(56) References Cited

OTHER PUBLICATIONS

Duban-Deweer et al., "Proteomic Analysis of Plasma Membrane Proteins in an In Vitro Blood-Brain Barrier Model", Proteomics—Human Diseases and Protein Functions, Feb. 10, 2012, pp. 397-398.
Gaur, "Prokaryotic and eukaryotic non-membrane proteins have biased amino acid distribution", J Comput Sci & Syst Biol 2.6 (2009): 298-299.
Green, "Avidin", Advances in protein chemistry 29 (1975): 85-133 (abstract only).
Maier et al., "Correlation of mRNA and protein in complex biological samples", FEBS letters 583.24 (2009): 3966-3973.
Ong et al., "Stable isotope labeling by amino acids in cell culture, SILAC, as a simple and accurate approach to expression proteomics", Molecular & cellular proteomics 1.5 (2002): 376-386.
International Application No. PCT/US2017/043273, "PCT Search Report", dated Nov. 3, 2017, 14 pages.
Wertz et al., "Influence of water on protein structure. An analysis of the preferences of amino acid residues for the inside or outside and for specific conformations in a protein molecule", Macromolecules 11.1 (1978): 9-15 (abstract only).

\* cited by examiner

FIG. 1 A
FIG. 1 B
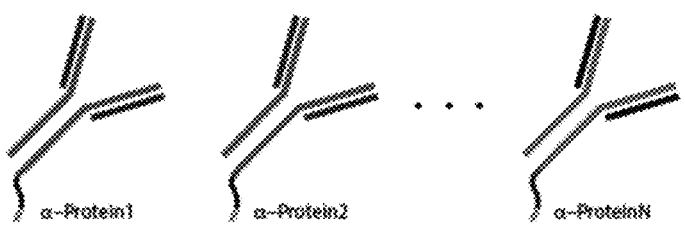
FIG. 1 C
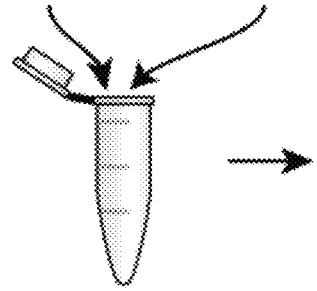
FIG. 1 D
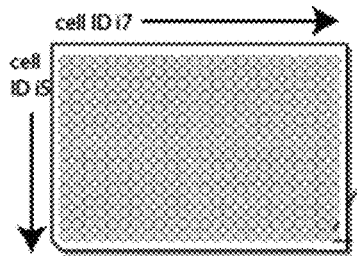
FIG. 1 E
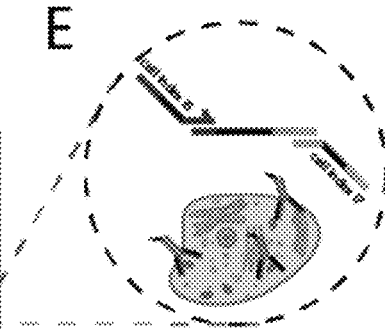

Maleimide-conjugated antibody vs. unconjugated antibody

Lysine-conjugated antibody vs. unconjugated antibody

SEQUENCE LISTING

<160> NUMBER OF SEQ ID NOS: 1

<210> SEQ ID NO 1
<211> LENGTH: 50
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 1
ggtagaagta ctagtacgct gtntcttata nacatctccg agcccacgag            50

QUANTITATIVE MASSIVELY PARALLEL PROTEOMICS

PRIOR RELATED APPLICATION

This application claims priority to U.S. Provisional Application No. 62/365,542 filed Jul. 22, 2016, which is hereby incorporated in its entirety by this reference.

FIELD

Embodiments of the present disclosure relate to the identification of an expression profile in a cell. In particular, compositions and methods for identifying an expression profile in a single cell and populations of cells are provided.

BACKGROUND

The ability to measure the relative amounts of molecules (e.g., proteins) in a cell enables deeper biological and clinical understanding. In particular, the ability to determine the relative abundance of the greater than 20,000 cellular proteins is desirable. Currently, the most widely used methods for proteomic detection are mass spectrometry and antibody staining. Mass spectrometry requires expensive instrumentation, is heavily biased towards abundant protein species, and produces only semi-quantitative data. Antibody detection usually requires less input material and is more quantitative. However, the most widely used antibody detection method (e.g., immunofluorescence-based flow cytometry) is not well-suited for multiplexed protein measurements because fluorescence spectral signatures on greater than forty antibodies in a mixture cannot be resolved. Recently developed methods for the detection of the proteome of single cells based on flow cytometry coupled to a mass spectrometer (CyTof) have partially addressed the throughput limitation for the detection of proteins from single cells, but these methods are extremely expensive, are not perfectly quantitative, and cannot be expanded beyond detection of about one hundred individual proteins. Therefore, compositions and methods for detection of proteins in single cells and populations of cells are necessary.

SUMMARY

Provided herein are methods for identifying an expression profile in a single cell or of a population of cells, including the step of contacting a population of cells with multiple antibodies under conditions that promote specific binding of the antibodies to target antigens of the cells, wherein each antibody is capable of binding to a unique target antigen of one or more cells, wherein each antibody is conjugated to an oligonucleotide, and wherein the oligonucleotide includes a unique molecular identifier sequence and an antibody identifier sequence corresponding to the unique target antigen. The method also may include separating single cells of the population into individual compartments. Also, the method may include amplifying the unique molecular identifier sequences and antibody identifier sequences in each individual compartment. Further, the method may include analyzing the amplified unique molecular identifier sequences and antibody identifier sequences to identify the expression profile of each single cell. In some embodiments, the population of cells may be fixed and permeabilized prior to contacting the population with multiple antibodies. In certain embodiments, each compartment further includes an oligonucleotide including a unique cellular identifier sequence that corresponds to the single cell in each compartment. In some embodiments, the individual compartment may be a well of a tissue culture plate or a microfluidic droplet. Additionally, the method may include quantifying the amplified unique molecular identifier sequences and antibody identifier sequences. Also, in some embodiments, analyzing the amplified unique molecular identifier sequences and antibody identifier sequences includes sequencing the amplified unique molecular identifier sequences and antibody identifier sequences. In certain embodiments, the antigen may be a protein, for example, a cell surface protein, an intracellular protein or an extracellular protein. In some embodiments, the method may be used to identify expression of two or more proteins.

Also provided are methods of identifying an expression profile of a population of cells including the step of contacting a population of cells with multiple antibodies under conditions that promote specific binding of the antibodies to the cells; wherein each antibody is capable of binding to a unique target antigen of one or more cells, wherein each antibody is conjugated to an oligonucleotide, and wherein the oligonucleotide includes a unique molecular identifier sequence and an antibody identifier sequence corresponding to the unique target antigen. The method also may include amplifying the unique molecular identifier sequences and antibody identifier sequences. Also, the method may include analyzing the amplified unique molecular identifier sequences and antibody identifier sequences to identify the expression profile of the population of cells. Additionally, the method may include quantifying the amplified unique molecular identifier sequences and antibody identifier sequences. Also, in some embodiments, analyzing the amplified unique molecular identifier sequences and antibody identifier sequences may include sequencing the amplified unique molecular identifier sequences and antibody identifier sequences. In some embodiments, the method may be used to identify expression of two or more proteins.

Further provided are methods of identifying an expression profile of a population of cells including the steps of lysing a population of cells and labeling the cellular proteins in the cell lysate with an affinity label. The method may further include contacting the affinity labeled proteins with beads including an agent that binds the affinity label to generate protein-coated beads. The method also may include contacting the protein-coated beads with multiple antibodies under conditions that promote specific binding of the antibodies to the protein-coated beads; wherein each antibody binds to a unique target protein, wherein each antibody is conjugated to an oligonucleotide, and wherein the oligonucleotide includes a unique molecular identifier sequence and an antibody identifier sequence corresponding to the unique target protein. The method may further include amplifying the unique molecular identifier sequences and antibody identifier sequences. The method also may include analyzing the amplified unique molecular identifier sequences and antibody identifier sequences to identify the expression profile of the population of cells. In certain embodiments, single cells of the population are separated into individual compartments prior to the lysing of the cells. In certain embodiments, each compartment further includes an oligonucleotide that includes a unique cellular identifier sequence that corresponds to the single cell in each compartment. In some embodiments, the individual compartment may be a well of a tissue culture plate or a microfluidic droplet. Additionally, the method may include quantifying the amplified unique molecular identifier sequences and antibody identifier sequences. Also, in some embodiments, analyzing the amplified unique molecular identifier sequences and antibody identifier sequences may include sequencing the amplified unique molecular identifier sequences and antibody identifier sequences. In some embodiments, the method may be used to identify expression of two or more proteins. In certain embodiments, the cells may be lysed with an agent that extracts proteins and nucleic acids (e.g., DNA and/or RNA) from the cell. Additionally, the method can include the step of analyzing the DNA to obtain genomic information and/or analyzing the RNA to obtain transcriptomic information.

Also provided are methods of identifying an expression profile and a transcriptional profile in a single cell of a population of cells including the step of contacting a population of cells with multiple antibodies under conditions that promote specific binding of the antibodies to the cells; wherein each antibody binds to a unique target antigen on the cell surface of one or more cells, wherein each antibody is conjugated to an oligonucleotide, and wherein the oligonucleotide includes (i) a unique molecular identifier sequence, (ii) an antibody identifier sequence corresponding to the unique target antigen, and (iii) a poly(dA) sequence. The method also may include encapsulating a single cell and a bead coated with poly (dT)-containing sequencing primers in a microfluidic droplet and allowing hybridization of the poly (dT)-containing sequence primers with the poly (dA) sequence of the oligonucleotide sequence conjugated to the antibodies and the poly (dA) sequences of mRNA transcripts in the encapsulated cell. The method also may include generating a cDNA library by reverse transcribing the primed mRNA transcripts in the cell. The method also may include amplifying the unique molecular identifier and antibody identifier sequences in the droplet. The method also may include analyzing the amplified unique molecular identifier sequences and antibody identifier sequences to identify at least one target antigen of the single cell, thus identifying the expression profile of the single cell. The method also may include sequencing the cDNA library to identify the transcriptional profile of the single cell. Additionally, the method may include quantifying the amplified unique molecular identifier sequences and antibody identifier sequences. Also, in some embodiments, analyzing the amplified unique molecular identifier sequences and antibody identifier sequences may include sequencing the amplified unique molecular identifier sequences and antibody identifier sequences. In some embodiments, the method may be used to identify expression of two or more proteins.

Further provided are kits for identifying an expression profile in a single cell or population of cells. The kits may include multiple antibodies, wherein each antibody is capable of binding to a unique target antigen, wherein each antibody is conjugated to an oligonucleotide, and wherein the oligonucleotide includes a unique molecular identifier sequence and an antibody identifier sequence corresponding to the unique target antigen. The kit also may include multiple oligonucleotide primers for amplification of the antibody identifier sequences. In some embodiments, each oligonucleotide primer includes a unique cellular identification sequence corresponding to a single cell.

DESCRIPTION OF THE DRAWINGS

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

FIG. 1A is an exemplary schematic of an antibody identifier sequence (antibody BC or antibody bar code) and a unique molecular identifier sequence (UMI) that may be conjugated to an antibody. The antibody identifier sequence and the unique molecular identifier sequence are flanked by primer sequences (UP1 and UP2).

FIG. 1B is an exemplary schematic of multiple antibodies, wherein each antibody is conjugated to an antibody identifier sequence corresponding to a unique target antigen and a unique molecular identifier sequence.

FIG. 1C is a schematic diagram depicting a population of cells being contacted with the antibodies of FIG. 1B to allow binding of the antibodies to target antigens.

FIG. 1D a schematic diagram depicting a 386 well tissue culture plate and identification numbers for each well. The identification numbers correspond to oligonucleotides that include a unique cellular identification sequences used to amplify the antibody identifier sequences in cells contacted with the population of antibodies of FIG. 1B.

FIG. 1E a schematic diagram depicting an exemplary cell that includes cellular target antigens (both intracellular and extracellular) bound to three antibodies conjugated to oligonucleotides. As shown in FIG. 1E, the antibody identifier sequences are amplified using the oligonucleotides that include a unique cellular identification sequence.

DETAILED DESCRIPTION

Figure 2:
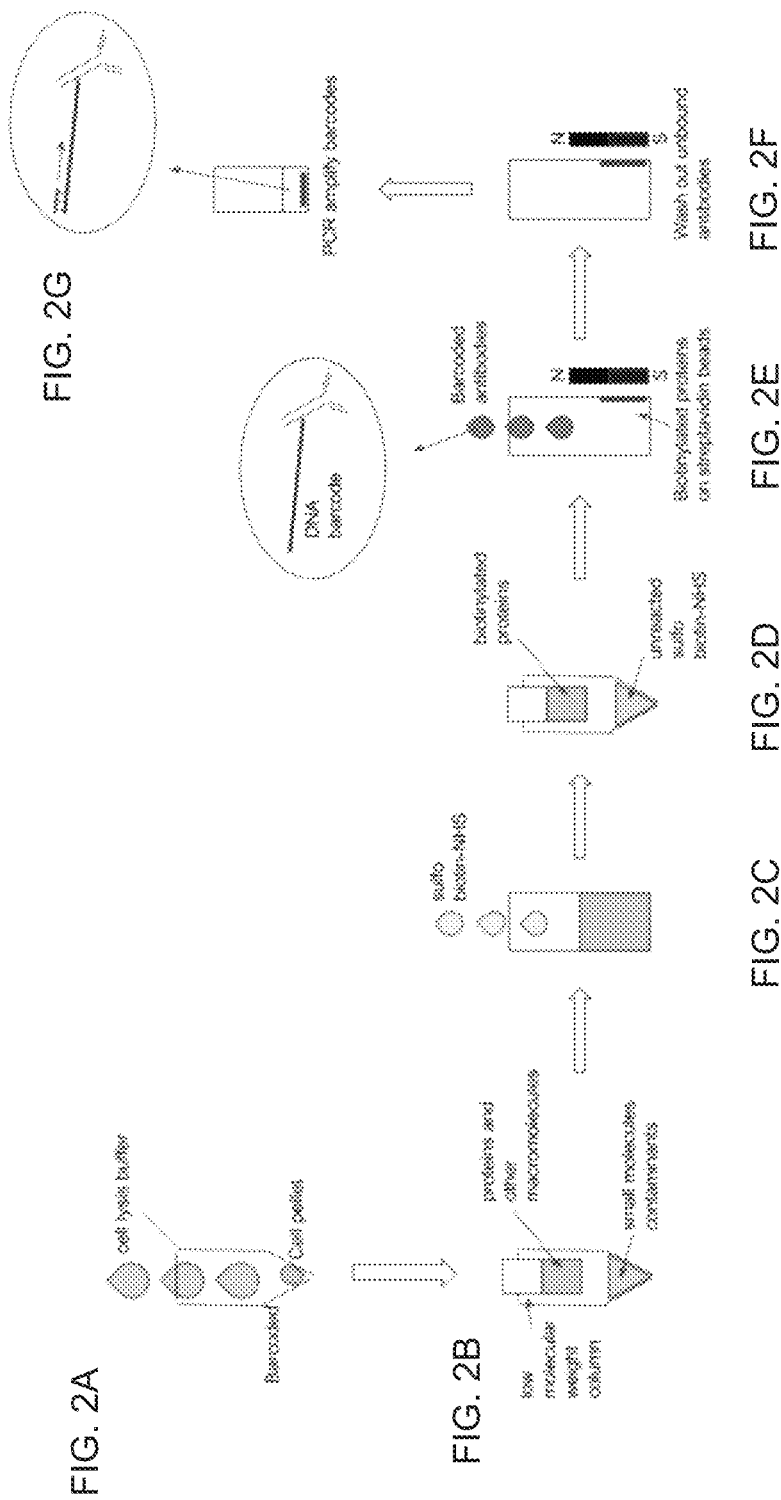
FIG. 2A is schematic diagram depicting centrifugation of cells to generate cell pellets followed by cell lysis.
FIG. 2B is a schematic diagram depicting removal of small nucleophilic, non-protein metabolites from the cell lysate that may interfere with a biotinylation reaction.
FIG. 2C is a schematic diagram depicting a reaction between cellular contents, including cellular proteins, and a reaction buffer that contains an excess concentration of sulfosuccinimido biotin (sulfo-NHS-biotin), which will react with any lysine side chain or the N-terminus of any protein.
FIG. 2D is a schematic diagram depicting a spin filtration step that removes unreacted sulfo-NHS-biotin.
FIG. 2E is a schematic diagram depicting capture of biotinylated proteins with streptavidin-coated magnetic beads and resuspension of the magnetic beads coated with biotinylated proteins in a buffer containing antibodies conjugated to oligonucleotides that include antibody identifier sequences.
FIG. 2F is a schematic diagram depicting removal of unbound antibodies.
FIG. 2G is a schematic diagram depicting PCR amplification of antibody identifier sequences to determine protein identities.

The following description recites various aspects and embodiments of the present compositions and methods. No particular embodiment is intended to define the scope of the compositions and methods. Rather, the embodiments merely provide non-limiting examples that are at least included within the scope of the disclosed compositions and methods. The description is to be read from the perspective of one of ordinary skill in the art; therefore, information well known to the skilled artisan is not necessarily included.

Provided herein are compositions and methods for identifying an expression profile in a single cell or a population of cells. Certain methods include the steps of a) contacting a population of cells with multiple antibodies under conditions that promote specific binding of the antibodies to target antigens of the cells; wherein each antibody is capable of binding to a unique target antigen in one or more cells, wherein each antibody is conjugated to an oligonucleotide, and wherein the oligonucleotide includes a unique molecular identifier sequence and an antibody identifier sequence corresponding to the unique target antigen; b) separating single cells of the population into individual compartments; c) amplifying the unique molecular identifier sequences and antibody identifier sequences in each individual compartment; and d) analyzing the amplified unique molecular identifier sequences and antibody identifier sequences to identify the expression profile of each single cell.

The expression profile of any cell(s), for example, a single cell or a population of cells, can be determined using any of the compositions and methods provided herein. For example, the cell can be a eukaryotic cell, a prokaryotic cell, an animal cell, a plant cell, a fungal cell, and the like. Optionally, the cell is a mammalian cell, for example, a human cell. The cell can be from a bodily fluid, tissue or organ. The cell also may be a primary cell, a germ cell, a stem cell or a precursor cell. The precursor cell can be, for example, a pluripotent stem cell or a hematopoietic stem cell. The expression profile of a cell in a particular phase of the cell cycle also may be determined. One of skill in the art would know how to synchronize cells to increase a proportion of cells in a particular phase prior to determination of the expression profile of the cell. The cell can be a cell from a healthy subject or a subject with a disease. In some embodiments, the population of cells is from one or more subjects. In some embodiments, the population of cells is a heterogeneous population of cells (i.e., a mixture of different cells types) or a homogeneous population of cells. In some embodiments, the population contains at least two different cell types. In some embodiments, the cells in the population include healthy and/or diseased cells from a thymus, white blood cells, red blood cells, liver cells, spleen cells, lung cells, heart cells, brain cells, skin cells, pancreas cells, stomach cells, cells from the oral cavity, cells from the nasal cavity, colon cells, small intestine cells, kidney cells, cells from a gland, brain cells, neural cells, glial cells, eye cells, reproductive organ cells, bladder cells, gamete cells, human cells, fetal cells, amniotic cells, or any combination thereof.

As used throughout, the term "subject" refers to an individual. Preferably, the subject is a mammal such as a primate, and, more preferably, a human of any age, including a newborn or a child. Non-human primates may be subjects as well. The term subject also may include domesticated animals (e.g., cats, dogs), livestock (e.g., cattle, horses, pigs, sheep, goats), and laboratory animals (e.g., ferret, chinchilla, mouse, rabbit, rat, gerbil, guinea pig). Thus, veterinary uses are contemplated herein.

As used throughout, an "expression profile" provides information about target antigens that are produced by a cell. The expression profile can be the expression profile of a single cell or the expression profile of a population of cells. As used throughout, the phrase "target antigens" may be, for example, proteins, lipids, or sugars. The expression profile can include the identity of one or more target antigens of the cell or the population of cells and/or the amount (relative or absolute) of one or more target antigens in the cell or the population of cells. The expression profile can also include the amount of a first target antigen relative to the amount of a different, second target antigen. The expression profile also may include information about target antigens that are not expressed by the cell or the population of cells. In some embodiments, the target antigen is a protein. The protein can be an intracellular protein, a cell-surface protein, or an extracellular protein. In some embodiments, the expression profile includes the identity and/or the amount of cell-surface proteins. In other embodiments, the expression profile includes the identity and/or the amount of cell-surface proteins and intracellular proteins. In other embodiments, the expression profile includes the identity and/or the amount of cell-surface proteins, intracellular proteins, and extracellular proteins. In some embodiments, the expression or two or more proteins are identified. For example, the expression of 10, 25, 50, 100, 200, 300, 400, 500, 600, 700, 800, 900, 1,000, 2,000, 3,000, 4,000, 5,000, 6,000, 7,000, 8,000, 9000, 10000, 20,000, or more proteins can be identified in the expression profile.

In some embodiments, an expression profile obtained using the methods provided herein can be used to diagnose a disease or condition in a subject or to determine how a subject will respond to treatment. In some embodiments, the presence of a specific expression profile associated with a particular disease or disorder may be used to diagnose and treat a subject with the disease or disorder. In other embodiments, the presence of a specific expression profile may be used to determine if the subject is at risk for developing the disease or disorder.

In some embodiments, the expression profile of a cell or a population of cells can be compared with a reference expression profile of a cell or a population of cells. For example, the expression profile of a cell or a population of cells that has been treated with an agent can be compared with the expression profile of a cell or a population of cells prior to treatment to determine if treatment has altered or modulated the expression profile of the cells or the population of cells. In another example, the expression profile of a cell or a population of cells from a subject being treated for a disease can be compared with the expression profile of a cell or a population of cells from a healthy subject that does not have the disease or the expression profile of a cell or a population of cells from a subject that has been successfully treated for the disease. In another example, the expression profile of a cell or a population of cells at a particular point in the cell cycle can be compared with the expression profile of a cell or a population of cells at a different point in the cell cycle.

In the methods provided herein, the population of cells may, in some embodiments, be sorted prior to or after contacting the population with the antibodies, for example, by fluorescence-activated cell sorting (FACS), to isolate one or more specific cell types from the population. Optionally, the cells can be sorted by expression of a specific marker. Optionally, the population of cells is a population wherein at least 90%, 95%, or 99% of the cells express a specific marker.

As used throughout, the phrase "multiple antibodies" means two or more antibodies. It is understood that the term "multiple" is used interchangeably with the phrase "a plurality of." As used herein, the term "antibody" encompasses, but is not limited to whole immunoglobulin (i.e., an intact antibody) of any class, including polyclonal and monoclonal antibodies. Fragments of antibodies that retain the ability to bind their specific antigens can also be used in the methods taught herein. Also useful in the methods provided herein are conjugates of antibody fragments and antigen binding proteins (single chain antibodies) as described, for example, in U.S. Pat. No. 4,704,692, the contents of which are hereby incorporated by reference in their entirety. In the methods provided herein, from two to about one thousand distinct antibodies can be used. By "distinct" is meant that each antibody binds a distinct target antigen epitope. For example, between about 2 to about 500 antibodies, between about 2 to about 10 antibodies, between about 10 to about 50 antibodies, between about 50 to about 100, between 100 to about 200, between 200 to about 300, between 300 to about 400, between 400 to about 500, or between 500 to about 1,000 distinct antibodies can be used in the methods provided. In the methods provided herein, the antibodies can be added to or brought into contact with the cell or a population of cells simultaneously or sequentially.

In some embodiments, the antibody may bind a particular covalent modification of a molecule, for example, a covalent modification of a protein. For example, the antibody can be an antibody that binds a phosphorylated amino acid on a protein or an antibody that binds a methylated or an acetylated amino acid on a protein. In another example, the antibody can be an antibody that binds a carbohydrate, lipid, acetyl group, formyl group, acyl group, SUMO protein, ubiquitin, Nedd, or prokaryotic ubiquitin-like protein on a protein of interest.

In the methods and compositions provided herein, antibodies are conjugated to an oligonucleotide. Oligonucleotides can be conjugated to antibodies by a number of methods known in the art (Kozlov et al. "Efficient strategies for the conjugation of oligonucleotides to antibodies enabling highly sensitive protein detection," *Biopolymers* 73(5): 621-630 (2004)). Aldehydes can be introduced to antibodies, for example, by modification of primary amines or oxidation of carbohydrate residues. Aldehyde- or hydrazine-modified oligonucleotides are prepared either during phosphoramidite synthesis or by post-synthesis derivatization. Conjugation between the modified oligonucleotide and antibody result in the formation of a hydrazone bond that is stable over long periods of time under physiological conditions. Oligonucleotides also may be conjugated to antibodies via thiol/maleimide chemistry, azide/alkyne chemistry, tetrazine/cyclooctyne chemistry, and other click chemistries. These chemical handles are prepared either during phosphoramidite synthesis or post-synthesis. As used herein, the term "click chemistry" refers to biocompatible reactions intended primarily to join substrates of choice with specific biomolecules. Click chemistry reactions are not disturbed by water, generate minimal and non-toxic byproducts, and are characterized by a high thermodynamic driving force that drives it quickly and irreversibly to high yield of a single reaction product, with high reaction specificity.

In the methods and compositions provided herein, the oligonucleotide conjugated to each antibody includes a unique molecular identifier sequence and an antibody identifier sequence. The unique molecular identifier sequence can be between about five to about fifty nucleotides in length. For example, the molecular identifier sequence can be between about 5 and about 10, between about 10 and about 20, between about 20 and about 30, between about 30 and about 40, or between about 40 and about 50 nucleotides in length. The term "unique molecular identifier sequence" refers to a sequence that can be used to identify a specific oligonucleotide through amplification and/or sequencing methods. The use of unique molecular identifier sequences (UMIs) for amplification and high throughput sequencing reduces bias in quantification of the sequences after amplification. Due to the high sequence diversity of UMIs, no two reads in the library should contain the same UMI, unless they are duplicated in the PCR process. Such duplicates are collapsed into one read so that an undistorted representation of the original pre-PCR library is obtained. Since the UMIs are part of the sequences of the oligonucleotides conjugated to the antibody, they are automatically incorporated into the sequencing library without additional tagging.

The term "antibody identifier sequence" refers to a sequence that corresponds to the unique target antigen that is bound by the antibody. This sequence can be used to identify the unique target antigen by using amplification and/or sequencing methods. The antibody identifier sequence can be between about five to about fifty nucleotides in length. For example, the antibody identifier sequence can be between about 5 and about 10, between about 10 and about 20, between about 20 and about 30, between about 30 and about 40, or between about 40 and about 50 nucleotides in length.

In certain embodiments, the population of cells is fixed and permeabilized prior to contacting the population with the multiple antibodies. Fixation should immobilize target antigens, including both intracellular and cell surface target antigens, while retaining cellular and subcellular structure. Fixation agents include, but are not limited to crosslinking agents, organic solvents and UV illumination. Non-limiting examples of a crosslinking agent include paraformaldehyde, formaldehyde (the non-polymerized version of paraformaldehyde), glutaraldehyde and disuccinimidyl glutarate. Non-limiting examples of organic solvents include, but are not limited to, ethanol, methanol, and acetone. In some embodiments, the fixation agent also serves as the permeabilization agent. For example, acetone and methanol can be used to simultaneously fix and permeabilize cells. In other embodiments, the permeabilization agent is used in combination with a fixation agent. Numerous detergents can be used to permeabilize cells. These include, but are not limited to, Triton X-100, Nonidet P-40 (NP-40), Tween 20, Saponin, Digitonin, and Leucoperm. One of skill in the art would know how to select a fixation agent and a permeabilization agent that immobilizes target antigens while allowing specific binding of the antibodies to the target antigens of the cells. In some embodiments, cells are permeabilized to allow staining of cellular proteins or other intracellular components and/or to allow hybridization of nucleic acids with probes and/or primers. In some embodiments, fixating and permeabilizing can be performed on adherent cells, for example, cells attached to a surface, such as a plate or a well in a tissue culture plate. After fixating and permeabilizing the cells, the cells can be trypsinized to detach the cells from a surface.

In some embodiments of the disclosed methods, single cells of the population of cells are separated into individual compartments. In some embodiments, separation of single cells into individual compartments includes distributing or sorting single cells into individual compartments. Optionally, the single cells can be lysed after separation into individual compartments. In any of the methods provided herein, single cells or populations of cells can be lysed with a solution containing a detergent, for example, and not to be limiting, Triton X-100, Triton-X114, NP-40, Brij-35, Brij-58, Tween 20, Tween 80, Octyl glucoside, Octyl thioglucoside, sodium dodecyl sulfate (SDS), CHAPS, and CHAPSO, to name a few. Cells can also be lysed by ultrasonication or by heating the cells to about 70-90° C.

The number of individual compartments can range from about 10 to about 100,000 individual compartments. One of skill in the art would know how to separate the population of cells to ensure that at least about 10%, 20%, 30%, 40%, 50%, 60%, 70%, 80%, or 90% of the individual compartments contain a single cell. Optionally, at least about 90%, 95%, or 99% of the individual compartments contain a single cell. Optionally, less than 25%, 10% or 5% of the individual compartments contain more than one cell. Optionally, each individual compartment containing a single cell further includes an oligonucleotide including a unique cellular identifier sequence that corresponds to the single cell in each compartment. In some embodiments, the cellular identifier sequence corresponds to a well in a tissue culture plate. In the methods set forth herein, the unique cellular identifier sequence is between about five and about fifty nucleotides in length. For example, the cellular identifier sequence can be between about 5 and about 10, between about 10 and about 20, between about 20 and about 30, between about 30 and about 40, or between about 40 and about 50 nucleotides in length. In some embodiments, the oligonucleotide including a unique cellular identifier sequence is used to amplify the unique molecular identifier sequence(s) and/or the antibody identifier sequence(s) in each compartment.

In some embodiments, one or more target antigens are identified by amplifying the antibody identifier sequences. Optionally, both the unique molecular identifier sequence and the antibody identifier sequences can be amplified. One of skill in the art would know how to design amplification primers that specifically amplify the unique molecular identifier sequence and/or the antibody identifier sequences. In certain embodiments, the amplification is performed using polymerase chain reaction (PCR), for example, quantitative PCR. In another embodiment, amplification of the antibody identifier sequences is performed using an oligonucleotide including a unique cellular identifier sequence that corresponds to a single cell in an individual compartment.

The methods provided herein include analyzing amplified molecular identifier sequences and/or antibody identifier sequences to identify the expression profile of the cell or population. Methods for analyzing nucleic acid sequences are known in the art. These include, but are not limited to, DNA sequencing, hybridization assays, microarray assays, primer extension assays, polymerase chain reaction (PCR) assays, including quantitative PCR, and ligase chain reaction assays.

In some embodiments, the unique molecular identifier sequences and antibody identifier sequences are optionally sequenced. Sequencing methods include, but are not limited to, shotgun sequencing, bridge PCR, Sanger sequencing (including microfluidic Sanger sequencing), pyrosequencing, massively parallel signature sequencing, nanopore DNA sequencing, single molecule real-time sequencing (SMRT) (Pacific Biosciences, Menlo Park, Calif.), ion semiconductor sequencing, ligation sequencing, sequencing by synthesis (Illumina, San Diego, Ca), Polony sequencing, 454 sequencing, solid phase sequencing, DNA nanoball sequencing, heliscope single molecule sequencing, mass spectroscopy sequencing, pyrosequencing, Supported Oligo Ligation Detection (SOLiD) sequencing, DNA microarray sequencing, RNAP sequencing, tunneling currents DNA sequencing, and any other DNA sequencing method identified in the future. One or more of the sequencing methods described herein can be used in high throughput sequencing methods. As used herein, the term "high throughput sequencing" refers to all methods related to sequencing nucleic acids where more than one nucleic acid sequence is sequenced at a given time Optionally, the amplification products from the individual compartments are pooled prior to sequencing. Optionally, the pooled sequencing results are deconvoluted using the unique cellular identifier sequences to identify the expression profile of a single cell associated with each unique cellular identifier sequence.

In some embodiments, the unique molecular identifier sequences and antibody identifier sequences are quantified and analyzed to identify an expression profile of single cells. Accordingly, some embodiments include quantifying the amplified unique molecular identifier sequences and antibody identifier sequences and correlating the quantified amplified unique molecular identifier sequences and antibody identifier sequences to the quantities of target antigens of interest in individual cells.

In the methods provided herein, the individual compartments may be, but are not limited to, wells of a tissue culture plate (e.g., microwells) or microfluidic droplets. As used herein the term "droplet" can also refer to a fluid compartment such as a slug, an area on an array surface, or a reaction chamber in a microfluidic device, such as for example, a microfluidic device fabricated using multilayer soft lithography (e.g., integrated fluidic circuits). Exemplary microfluidic devices also include the microfluidic devices available from 10× Genomics (Pleasanton, Calif.).

Relatively small droplets can be used in the methods provided herein. In some embodiments, the average diameter of the droplets may be less than about 5 mm, less than about 4 mm, less than about 3 mm, less than about 1 mm, less than about 500 micrometers, or less than about 100 micrometers. The "average diameter" of a population of droplets is the arithmetic average of the diameters of each of the droplets. In the methods provided herein, the droplets may be of the same shape and/or size, or of different shapes and/or sizes, depending on the particular application. In some embodiments, the individual droplets have a volume of about 1 picoliter to about 100 nanoliters.

A droplet generally includes an amount of a first sample fluid in a second carrier fluid. Any technique known in the art for forming droplets may be used. An exemplary method involves flowing a stream of the sample fluid containing the target material (e.g., antibody-labeled cells) such that the stream of sample fluid intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets containing the target material. The carrier fluid may be any fluid that is immiscible with the sample fluid. An exemplary carrier fluid is oil. Optionally, the carrier fluid includes a surfactant or is a fluorous liquid. Optionally, the droplets contain an oil and water emulsion.

Oil-phase and/or water-in-oil emulsions allow for the compartmentalization of reaction mixtures within aqueous droplets. The emulsions can comprise aqueous droplets within a continuous oil phase. The emulsions provided herein can be oil-in-water emulsions, wherein the droplets are oil droplets within a continuous aqueous phase.

In any of the methods provided herein, droplets containing cells optionally may be sorted according to a sorting operation prior to merging with one or more reagents (e.g., as a second set of droplets). In some embodiments, a cell can be encapsulated together with one or more reagents in the same droplet, for example, biological or chemical reagents, thus eliminating the need to contact a droplet containing a cell with a second droplet containing one or more reagents. Additional reagents may include reverse transcriptase enzymes, including enzymes with terminal transferase activity, primers, and oligonucleotides. In some embodiments, the droplet that encapsulates the cell already contains one or more reagents prior to encapsulating the cell in the droplet. In yet other embodiments, the reagents are injected into the droplet after encapsulation of the cell in the droplet. In some embodiments, the one or more reagents may contain reagents or enzymes such as a detergent that facilitates the breaking open of the cell and release of the cellular material therein. Once the reagents are added to the droplets containing the cells, the unique molecular identifier sequences and/or antibody identifier sequences can be amplified in the droplet, for example, by polymerase chain reaction (PCR). Alternatively, the cells may be lysed in the droplet prior to amplification of the unique molecular identifier sequences and/or antibody identifier sequences.

In some embodiments, a microfluidic device is used to generate single cell droplets, for example, a single cell emulsion droplet. The microfluidic device ejects single cells in aqueous reaction buffer into a hydrophobic oil mixture. The device can create thousands of droplets per minute. In some cases, a relatively large number of droplets can be generated, for example, at least about 10, at least about 30, at least about 50, at least about 100, at least about 300, at least about 500, at least about 1,000, at least about 3,000, at least about 5,000, at least about 10,000, at least about 30,000, at least about 50,000, or at least about 100,000 droplets. In some cases, some or all of the droplets may be distinguishable, for example, on the basis of oligonucleotide present in at least some of the droplets (e.g., which may include one or more unique sequences or barcodes). In some cases, at least about 50%, at least about 60%, at least about 70%, at least about 80%, at least about 90%, at least about 95%, at least about 97%, at least about 98%, or at least about 99% of the droplets may be distinguishable.

In one example, after the droplets are created, the device ejects the mixture of droplets into a trough. The mixture can be pipetted or collected into a standard reaction tube for thermocycling and PCR amplification. Single cell droplets in the mixture can also be distributed into individual wells, for example, into a multiwell plate for thermocycling and PCR amplification in a thermal cycler. After amplification, the droplets can be analyzed to identify target antigens in each single cell. In some embodiments, the cells are lysed inside the droplet before or after amplification. In other embodiments, the droplets can be distributed onto a chip for amplification. It is understood that numerous methods of generating droplets and amplifying nucleic acids therein are known in the art. See, for example, Abate et al., "DNA sequence analysis with droplet-based microfluidic," Lab Chip 13: 4864-4869 (2013); and Kaler et al. "Droplet microfluidics for Chip-Based Diagnostics," Sensors 14(12): 23283-23306 (2014)), both of which are incorporated herein in their entireties by this reference.

In some embodiments, fixed and permeabilized cells are encapsulated into droplets, and amplification of the fixed, permeabilized cells occurs in the droplets. In some embodiments, after thermocycling and PCR, the amplified products can be recovered from the droplet using numerous techniques known in the art. For example, ether can be used to break the droplet and create an aqueous/ether layer which can be evaporated to recover the amplification products. Other methods include adding a surfactant to the droplet, flash-freezing with liquid nitrogen and centrifugation. In some embodiments, once the amplification products are recovered, the products are further amplified and/or sequenced.

Also provided is a method of identifying an expression profile of a population of cells. The method includes the steps of: a) contacting a population of cells with multiple antibodies under conditions that promote specific binding of the antibodies to the cells; wherein each antibody in the plurality is capable of binding to a unique target antigen in one or more cells, wherein each antibody is conjugated to an oligonucleotide, and wherein the oligonucleotide includes a unique molecular identifier sequence and an antibody identifier sequence corresponding to the unique target antigen; b) amplifying the unique molecular identifier sequences and antibody identifier sequences; and c) analyzing the amplified unique molecular identifier sequences and antibody identifier sequences to identify the expression profile of the population of cells.

Optionally, the population of cells can be fixed and permeabilized as described above. Optionally, after contacting the population of fixed and permeabilized cells with the multiple antibodies, the cells can be lysed prior to amplification and analysis of the unique molecular identifier sequences and antibody identifier sequences to identify an expression profile of the population of cells. In some embodiments, the expression of two or more target antigens is identified. In embodiments where the population of cells is not lysed, the expression profile identifies expression of cell surface target antigens. In embodiments where a population of fixed and permeabilized cells is lysed, the expression profile identifies expression of cell surface target antigens and intracellular target antigens. In some embodiments, the target antigens may be proteins. In other embodiments, the target antigens may be lipids or sugars. It is understood that, in the methods provided herein, identifying expression includes identifying reduced or the absence of expression of one or more proteins.

Also provided is a method of identifying an expression profile for the cellular proteins of a population of cells. This method includes the steps of: a) lysing a population of cells; b) labeling the cellular proteins in the cell lysate of step a) with an affinity label; c) contacting the affinity labeled proteins with beads including an agent that binds the affinity label to generate protein-coated beads; d) contacting the protein-coated beads with multiple antibodies under conditions that promote specific binding of the antibodies to the protein-coated beads; wherein each antibody binds to a unique target protein, wherein each antibody is conjugated to an oligonucleotide, and wherein the oligonucleotide includes a unique molecular identifier sequence and an antibody identifier sequence corresponding to the unique target protein; e) amplifying the unique molecular identifier sequences and antibody identifier sequences; and f) analyzing the amplified unique molecular identifier sequences and antibody identifier sequences to identify the expression profile for the cellular proteins of the population of cells.

In some embodiments of these methods, the cellular proteins in the cellular material released from the lysed cells are labeled with an affinity label. In certain embodiments, the affinity label is a peptide tag. In other embodiments, the affinity label is a covalent peptide tag. In some embodiments, the affinity label is a protein tag. Other affinity tags include, but are not limited to, chitin binding protein-tag, maltose binding protein-tag, glutathione-S-transferase-tag, polyhistidine (His-tag), FLAG-tag, V5 tag, VSV-tag, Myc-tag, c-Myc-tag, HA-tag, E-tag, S-tag, SBP-tag, Softag 1, Softag 3, Strep-tag, TC tag, calmodulin-tag, Avi-tag, Xpress tag, isopeptag, Spy-tag, biotin carboxyl carrier protein (BCCP), green fluorescent protein-tag, HaloT-tag, Nus-tag, Fc-tag, Ty tag, thioredoxin-tag, or poly(NANP). In another embodiment, the affinity label is biotin or desthiobiotin. In some aspects, the biotinylated proteins are contacted with streptavidin. In another aspect, the biotinylated proteins are contacted with beads coated with streptavidin to form biotinylated protein-coated beads.

In some embodiments, single cells of the population are separated into individual compartments prior to the lysing of the cells. In certain embodiments, the lysis of single cells of the population, the biotinylation of cellular proteins, the contacting with beads, and the contacting with multiple antibodies conjugated with oligonucleotides is performed in individual compartments to determine the expression profile for cellular proteins of single cells in a population. One of skill in the art would know how to distribute beads into individual compartments such that each individual compartment includes a single cell and a single bead. In some embodiments, at least about 90%, about 95%, or about 99% of the individual compartments contain at least a single cell and at least a single bead. In other embodiments, about 90%, about 95%, or about 99% of the individual compartments contain a single cell and a single bead. Optionally, less than about 25%, about 10%, or about 5% of the individual compartments contain more than one cell and/or more than one bead. In some embodiments, amplification of the unique molecular identifier sequence and an antibody identifier sequence is performed in individual single cell compartments. In some embodiments, the amplified products are recovered from the individual compartments and optionally, further amplified and/or sequenced.

In any of the methods described herein, wherein the compartment is a droplet, a microfluidic device can be used to encapsulate a bead and a single cell in a droplet. In some embodiments, at least about 90%, about 95%, or about 99% of the droplets contain a single cell and a single bead. Optionally, less than about 25%, about 10%, or about 5% of the droplets contain more than one cell and/or more than one bead. For example, and not to be limiting, a microfluidic device can inject beads into single cell droplets to form multiple droplets, wherein each droplet contains a bead and a single cell. In another example, droplets containing a single cell can be merged with droplets containing a single bead to form multiple droplets containing a single cell and a single bead. In the methods provided herein, the bead or microbead is a gel bead that can be dissolved once inside an individual compartment, for example, a droplet. The bead can be plastic (such as polystyrene), glass, silica, latex, metallic, or any other suitable substance having a substantially spherical shape with less than 5 mm in diameter. In certain aspects, the bead is magnetic.

Optionally, each individual compartment containing a single cell and a single bead further includes an oligonucleotide including a unique cellular identifier sequence that corresponds to the single cell in each compartment. In some embodiments, the cellular identifier sequence corresponds to a well in a tissue culture plate. In some embodiments, the oligonucleotide including a unique cellular identifier sequence is used to amplify the unique molecular identifier sequence and/or the antibody identifier sequence in each compartment.

In some embodiments, the target antigen is identified by amplifying the antibody identifier sequences. Optionally, both the unique molecular identifier sequence and the antibody identifier sequences can be amplified. One of skill in the art would know how to design amplification primers that specifically amplify the unique molecular identifier sequence and/or the antibody identifier sequences. In certain embodiments, the amplification is performed using polymerase chain reaction (PCR), for example, quantitative PCR. In another embodiment, amplification of the antibody identifier sequences is performed using an oligonucleotide including a unique cellular identifier sequence that corresponds to a single cell in an individual compartment.

The methods provided herein include analyzing amplified molecular identifier sequences and/or antibody identifier sequences. Methods for analyzing nucleic acid sequences are known in the art. These include, but are not limited to, DNA sequencing, hybridization assays, microarray assays, primer extension assays, polymerase chain reaction (PCR) assays, and ligase chain reaction assays.

In some embodiments, the unique molecular identifier sequences and antibody identifier sequences are optionally sequenced. Sequencing methods include, but are not limited to, high throughput sequencing, Sanger sequencing, pyrosequencing, massively parallel signature sequencing, nanopore DNA sequencing, single molecule real-time sequencing (SMRT) (Pacific Biosciences, Menlo Park, Calif.), ion semiconductor sequencing, ligation sequencing, sequencing by synthesis (Illumina, San Diego, Ca), polony sequencing, solid phase sequencing, DNA nanoball sequencing, heliscope single molecule sequencing, mass spectroscopy sequencing, DNA microarray sequencing, and any other DNA sequencing method identified in the future. Optionally, the amplification products from the individual compartments are pooled prior to sequencing. Optionally, the pooled sequencing results are deconvoluted using the unique cellular identifier sequences to identify the expression profile of a single cell associated with each unique cellular identifier sequence.

In some embodiments, the unique molecular identifier sequences and antibody identifier sequences are quantified and analyzed to identify an expression signature of single cells or populations of cells. Accordingly, some embodiments include quantifying the amplified unique molecular identifier sequences and antibody identifier sequences and correlating the quantified amplified unique molecular identifier sequences and antibody identifier sequences to the quantities of target antigens of interest in individual cells or populations of cells.

The methods provided herein may comprise lysing a population of cells or individual cells with an agent that extracts proteins and nucleic acids from the cells. The nucleic acids can comprise DNA and/or RNA. In some embodiments, DNA extracted from the cells is analyzed to obtain genomic information. In other embodiments, RNA extracted from the cells is analyzed to obtain transcriptomic information. The expression profiles obtained with the methods described herein can also include genomic and/or transcriptomic information for a single cell or a population of cells.

Also provided is a method of identifying an expression profile and a transcriptional profile in a single cell or a population of cells. This method includes the steps of: a) contacting a population of cells with multiple antibodies under conditions that promote specific binding of the antibodies to the cells; wherein each antibody binds to a unique target antigen of one or more cells, wherein each antibody is conjugated to an oligonucleotide, and wherein the oligonucleotide includes (i) a unique molecular identifier sequence, (ii) an antibody identifier sequence corresponding to the unique target antigen, and (iii) a poly(dA) sequence; encapsulating a single cell and a bead coated with poly (dT)-containing sequencing primers in a microfluidic droplet; c) allowing hybridization of the poly (dT)-containing sequence primers with the poly (dA) sequence of the oligonucleotide sequence conjugated to the antibodies and the poly (dA) sequences of mRNA transcripts in the encapsulated cell; d) generating a cDNA library by reverse transcribing the primed mRNA transcripts in the cell; e) amplifying the unique molecular identifier and antibody identifier sequences in the droplet; f) analyzing the amplified unique molecular identifier sequences and antibody identifier sequences to identify at least one target antigen in the single cell, thus identifying the expression profile of the single cell; and g) sequencing the cDNA library to identify the transcriptional profile of the single cell.

In some embodiments, the population of cells is fixed and permeabilized, as described above, prior to contacting the population with the multiple antibodies. When the cells are fixed and permeabilized, the antibodies can bind to intracellular and cell-surface target antigens.

Figure 3:
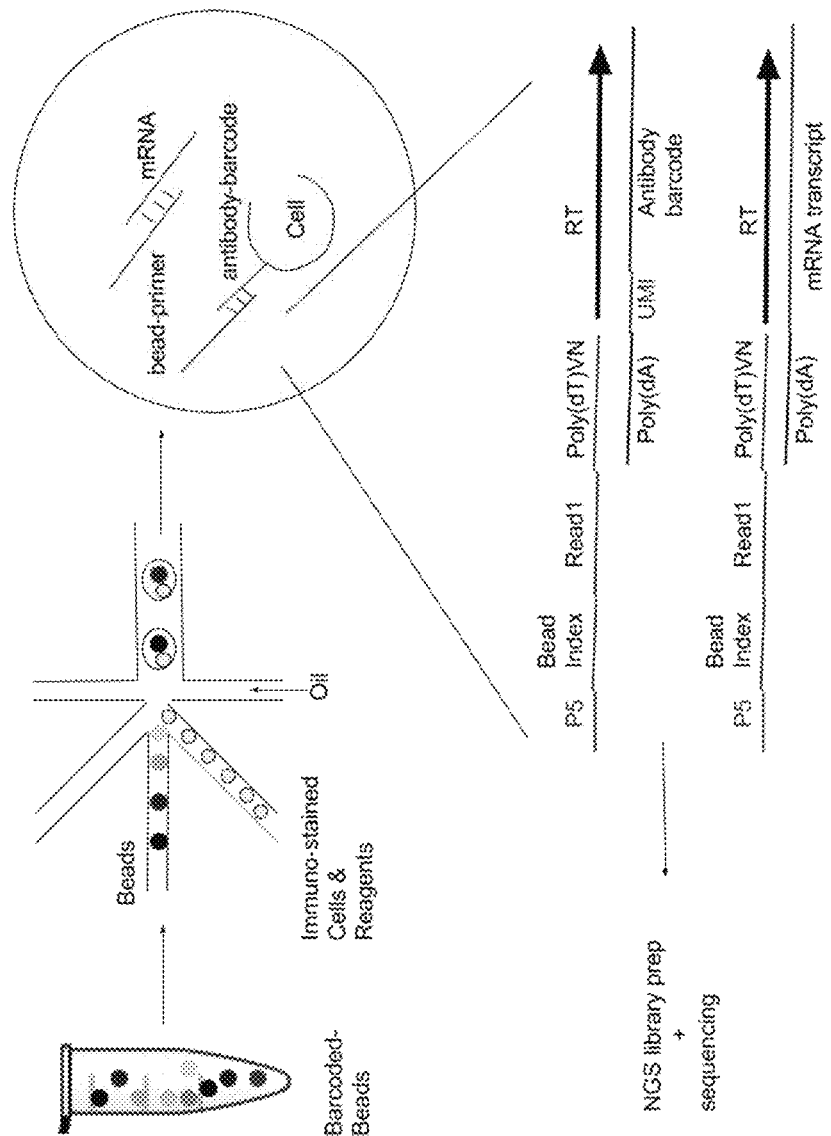
FIG. 3 is an exemplary schematic diagram showing simultaneous single-cell protein expression analysis and transcriptome analysis in microfluidic droplets using the methods and compositions described herein.

This method allows simultaneous single-cell proteomic and transcriptome analysis (FIG. 3). In this embodiment, the high-throughput loading capacity of microfluidic encapsulation devices is leveraged to trap a single bead coated with poly (dT)-containing sequencing primers and a cell in a droplet. In other embodiments, a single cell and a bead coated with poly (dT)-containing sequencing primers may be contained in other types of individual compartments, for example, in a microwell.

Beads can be coated with oligonucleotide sequences by a number of methods commonly known in the art. For example, beads can be conjugated using carboxyl and/or amino groups on the bead surface to be used for covalent coupling of the oligonucleotide to the bead (e.g., an amine-modified oligonucleotide can be reacted with a carboxylate-modified bead using carbodiimide chemistry). Other chemistries that can be used for covalent coupling of oligonucleotides to bead surfaces include, but are not limited to, chemistries involving, primary aliphatic amines, aromatic amines, chloromethyl, amide, hydrazide, aldehyde, hydrozyl, thiol or epoxy groups, wherein the bead and/or the oligonucleotide are modified to perform the coupling of the oligonucleotide to the bead. Beads also can be coated with oligonucleotides using streptavidin and biotin interaction. For example, microbeads coated with avidin or streptavidin can be bound to biotin-conjugated oligonucleotides.

In some embodiments, the cell or population of cells to be profiled can be stained with antibodies conjugated with oligonucleotide sequences including an antibody identifier sequence and a poly(dA) sequence, and the bead is coated with oligonucleotides comprising high-throughput sequencing primers and a poly(dT) sequence. In certain aspects, the oligonucleotide also comprises a bead index sequence corresponding to the individual bead, and since the oil droplet contains a single cell and bead, the bead index also corresponds to an individual cell. In certain aspects, the bead can be dissolved inside an oil droplet, releasing the oligonucleotides from the beads and allowing liquid-phase hybridization of primers comprising poly(dT) with both the oligonucleotide sequences comprising poly(dA) and cellular mRNA transcripts that terminate naturally with poly(A) tails.

In other embodiments, beads conjugated to distinct oligonucleotides may be labeled with specific fluorescent dye combinations to uniquely label each bead and encode bead identity.

In some embodiments, a library of beads conjugated to oligonucleotide sequences can be used for simultaneous detection of protein and mRNA. The library of beads can be created by coating beads with high-throughput sequencing primers including a sequence complementary to a specific mRNA and a sequence corresponding to the target antigen recognized by the antibody.

In certain embodiments, the sequencing is performed using sequencing primers comprising a poly(dT) sequence and wherein the oligonucleotide conjugated to the antibody also comprises a poly(dA) sequence. In certain embodiments, the sequencing primers are bound to beads. In other embodiments, the sequencing primers also comprise a bead index sequence.

In certain embodiments, the mRNA and the oligonucleotides conjugated to the antibodies are sequenced. In certain other embodiments, the mRNA and the oligonucleotides conjugated to the antibodies are sequenced simultaneously. In certain aspects, the mRNA is converted to a double stranded DNA prior to sequencing. In yet another embodiment, if only sequencing results from antibody binding are desired and not mRNA, RNase A can be added with cells loaded into the microfluidic device to neutralize mRNA content.

Also provided herein is a kit for identifying an expression profile in a single cell or population of cells. The kit may include: a) multiple antibodies, wherein each antibody is capable of binding to a unique target antigen, wherein each antibody is conjugated to an oligonucleotide, and wherein the oligonucleotide includes a unique molecular identifier sequence and an antibody identifier sequence corresponding to the unique target antigen; and b) multiple oligonucleotide primers for amplification of the antibody identifier sequence.

In some embodiments, the oligonucleotide primers for amplification of the antibody identifier sequence include a unique cellular identification sequence corresponding to a single cell. The cellular identification sequence can be about five to about fifty nucleotides in length. For example, the cellular identification sequence can be between about 5 and about 10, between about 10 and about 20, between about 20 and about 30, between about 30 and about 40, or between about 40 and about 50 nucleotides in length. In some embodiments, the kit includes between two and about one thousand antibodies. For example, between about 2 to about 500 antibodies, between about 2 to about 10 antibodies, between about 10 to about 50 antibodies, between about 50 to about 100, between 100 to about 200, between 200 to about 300, between 300 to about 400, between 400 to about 500, or between 500 to about 1,000 distinct antibodies can be used in the methods provided. In the kits provided herein, the unique molecular identifier sequence can be about five to about fifty nucleotides in length. For example, the molecular identifier sequence can be between about 5 and about 10, between about 10 and about 20, between about 20 and about 30, between about 30 and about 40, or between about 40 and about 50 nucleotides in length. In the kits provided herein, the antibody identifier sequence can be about five to about fifty nucleotides in length. For example, the antibody identifier sequence can be between about 5 and about 10, between about 10 and about 20, between about 20 and about 30, between about 30 and about 40, or between about 40 and about 50 nucleotides in length.

Optionally, the kit contains multiple antibodies, wherein each antibody is conjugated to an oligonucleotide, wherein the oligonucleotide includes (i) a unique molecular identifier sequence, (ii) an antibody identifier sequence corresponding to the unique target antigen, and (iii) a poly(dA) sequence. In some embodiments, the kit further includes multiple beads, wherein the beads are conjugated to poly (dT)-containing sequencing primers. The kits described herein can also include instructions for use.

Disclosed are materials, compositions, and components that can be used for, can be used in conjunction with, can be used in preparation for, or are products of the disclosed embodiments. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules included in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties. The following description provides further non-limiting examples of the disclosed compositions and methods.

EXAMPLES

Example 1

Detection of a Protein Expression Profile from Individual Cells.

An antibody library is constructed using the antibody clones used in the Fluidigm® Cytof® human reactive antibody panels for cell cycle and proliferation (panel number 201313), signaling 1 (panel number 201309), embryonic stem cell/induced pluripotent stem cell (panel number 201320) and intracellular cytokine panel (panel number 201308) for a total of 29 antibodies (FIGS. 1A and 1B). The unique molecular identifier sequences are synthesized using mixed primers to create random, unique oligonucleotide sequences 20 nucleotides in length. An antibody identifier sequence 20 nucleotides in length that is specific for each distinct antibody clone in the library is created by extending from the unique molecular identifier sequence using specific primers for each distinct antibody in the next step of the oligonucleotide synthesis reaction. Finally, sequences complementary to Illumina® sequencing primers are synthesized and added to the unique molecular identifier sequence and antibody identifier sequence. The oligonucleotides are conjugated to the antibodies by introducing aldehydes to the antibodies by modification of primary amines. Aldehyde-modified oligonucleotides or hydrazine-modified oligonucleotides are prepared either during phosphoramidite synthesis or by post-synthesis derivatization. Conjugation between the modified oligonucleotide and antibody results in the formation of a hydrazone bond. Alternatively, the oligonucleotides are conjugated to the antibodies via thiol/maleimide chemistry.

Figures 6A, 6B:
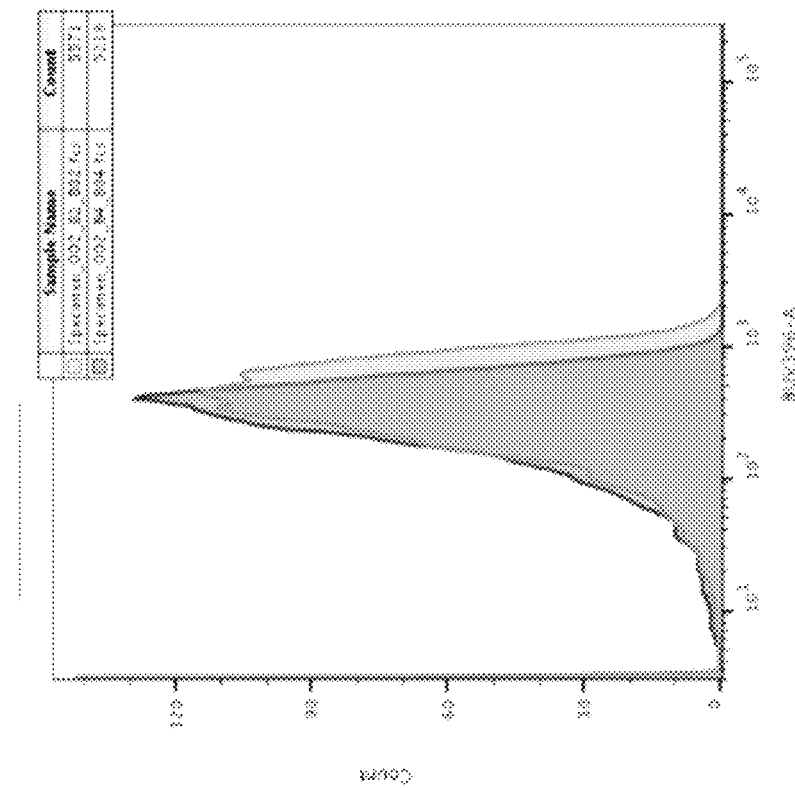
FIG. 6A shows the results of a competition assay where PBMCs were stained with a detection antibody (CD3-BUV396 antibody) and either unconjugated antibodies or maleimide conjugated antibodies were added to compete with the detection antibody. The light gray curve shows the results observed when the maleimide conjugated antibody was used to compete with the detection antibody, and the medium gray curve shows the results observed when the unconjugated antibody was used to compete. When increasing doses of unconjugated or oligo-conjugated CD3 antibodies of the same clone were added to the mixture, the maleimide conjugated antibody competed with the detection antibody as effectively as the unconjugated antibody, indicating that the chemistry did not affect antibody function.
FIG. 6B shows the results of a competition assay where PBMCs were stained with a detection antibody (CD3-BUV396 antibody) and either unconjugated or lysine conjugated antibodies were added to compete with the binding of the detection antibody to the cells. The light gray curve (two peaks) shows the results observed when the lysine conjugated antibody was used to compete with the detection antibody, and the medium gray curve (single peak) shows the results observed when the unconjugated antibody was used to compete. In contrast to the results obtained with maleimide conjugated antibody, when increasing doses of unconjugated or oligo-conjugated CD3 antibodies of the same clone were added to the mixture, the lysine-conjugated antibody did not compete as effectively against the detection antibody as the unconjugated antibody, leaving a significant portion of cells that still stained positive.

Conjugation of oligonucleotides to antibodies using thiol/maleimide chemistry can be carried out by essentially following the protocol for the Maxpar Antibody Labeling kit (Fluidigm, (South San Francisco, Calif.)), and substituting the metal polymer with a sulfo-SMCC (sulfosuccinimidyl 4-(N-maleimidomethyl)cyclohexane-1-carboxylate) activated oligo (Thermo Fisher Scientific, (Waltham, Mass.)). Alternatively, antibodies can be conjugated to sulfo-SMCC activated streptavidin protein, and oligonucleotides can be easily installed to streptavidin-antibody conjugates by a simple 30 minute incubation in PBS using a 1:1 ratio with high labeling efficiency. This latter approach allows production of a bulk conjugate preparation, and different oligonucleotide sequences, for example, biotin-modified oligonucleotides can be conveniently exchanged without the need to prepare different oligonucleotide-antibody conjugates each time. As shown in FIGS. 6A and 6B, in contrast to oligonucleotide conjugation using lysine chemistry (FIG. 6B), antibodies labeled with maleimide chemistry (FIG. 6A) fully conserve antigen-affinity.

The antibody library of 29 antibodies, wherein each antibody is conjugated to an oligonucleotide including a unique molecular identifier sequence and antibody identifier sequence, is added to HeLa cells (FIGS. 1A-1C). The antibody library is resuspended in a staining buffer that promotes solubility and specific binding of the antibodies to their cognate antigen.

The cells are pooled, washed in PBS to remove unbound antibodies, and the cells are plated using a flow cytometer into individual wells of a 96 well tissue culture plate (FIG. 1D-E). Cellular identifier primers corresponding to the location of each individual well, dNTPs and DNA polymerase are added to each well, and PCR is performed to amplify the oligonucleotide sequences conjugated to the antibodies bound to the surface of the cells.

The amplified sequences from the 96 well plate are then pooled and collected using biotinylated probes complementary to the antibody identifier sequence. The collected oligonucleotides are then sequenced using Illumina sequencing primers in Illumina sequencing methods.

Example 2

Detection of Intracellular Proteins Using Biotin Affinity Tags

HeLa cells are centrifuged at 1,000 RPM in a microcentrifuge at 4° C. for 5 minutes to generate cell pellets (FIG. 2A). The cell pellets are washed in ice-cold PBS at 4° C. and then lysed using high salt radioimmunoprecipitation assay (RIPA) buffer containing 1% SDS so that all soluble and membrane bound protein contents are extracted and their native epitopes preserved. Small nucleophilic, non-protein metabolites that may interfere with the biotinylation reaction are washed out using a spin filtration column with a small molecular weight cutoff (FIG. 2B).

The retained proteins and cellular contents are reconstituted in a reaction buffer that contains an excess concentration of sulfosuccinimido biotin (sulfo-NHS-biotin), which will react with any lysine sidechain or the N-terminus of any protein via a well-established nucleophilic substitution reaction (FIG. 2C). Lysine residues are found abundantly (~6% of amino acids) in proteins and are generally solvent exposed. The excess concentration of sulfo-NHS-biotin drives the chemical reaction quickly to completion. Another spin filtration step removes unreacted sulfo-NHS-biotin (FIG. 2D). The resulting biotinylated proteins are then bound to streptavidin-coated magnetic beads. The beads are captured by a magnet and contaminants and unbound material are easily washed away in this biomagnetic separation process (FIG. 2E). Magnetic beads coated with biotinylated proteins are then resuspended in a staining buffer containing the antibody library described in Example 1 including distinct antibodies conjugated to oligonucleotides. Afterwards, unbound antibodies are washed away with another biomagnetic separation (FIG. 2F).

In the final step, antibody identifier sequences are amplified by a polymerase chain reaction (PCR) and sequenced by Illumina® next generation sequencing to determine protein identities and concentrations (FIG. 2G).

Example 3

Simultaneous Single-Cell Immuno Profiling and Expression Analysis

Microfluidic encapsulation devices are obtained from 10× Genomics™ and are used to isolate individual cells and beads inside individual oil droplets (FIG. 3). Individual HeLa cells are permeabilized and stained with antibodies each conjugated with an antibody identifier identifier sequence, a unique molecular identifier sequence, and a poly(dA) sequence. Antibody libraries, as described in Example 1, are constructed, and oligonucleotides are conjugated to the individual libraries as described in Example 1. Individual gel beads are coated with Illumina® high-throughput sequencing primers including a unique bead index sequence and a poly(dT) capture sequence. The oligonucleotides are conjugated to the gel beads using amine-modified oligonucleotides that are reacted with carboxylate-modified gel microbeads using carbodiimide chemistry. The stained HeLa cells and oligonucleotide coated gel beads are mixed with an oil-surfactant solution to trap individual cells and beads inside individual oil droplets. The gel beads are dissolved and liquid-phase hybridization of poly(dT) primers with both the antibody identifier sequences that include poly(dA) sequences and cellular mRNA transcripts occurs. After hybridization, the beads bound to antibodies and mRNA transcripts are collected and washed. The hybridized and primed oligonucleotides are then converted to double-stranded DNA using reverse transcription. The double-stranded DNA is then further processed into a next generation sequencing library and sequenced using the Illumina® next generation sequencing method. The immuno-profiles and transcriptomes of the HeLa cells are then determined by analyzing the number of sequence reads corresponding to individual antibody types and mRNA transcript sequences corresponding to the cognate antigens of the antibodies.

Example 4

Identification of Target Antigens

Figure 4:
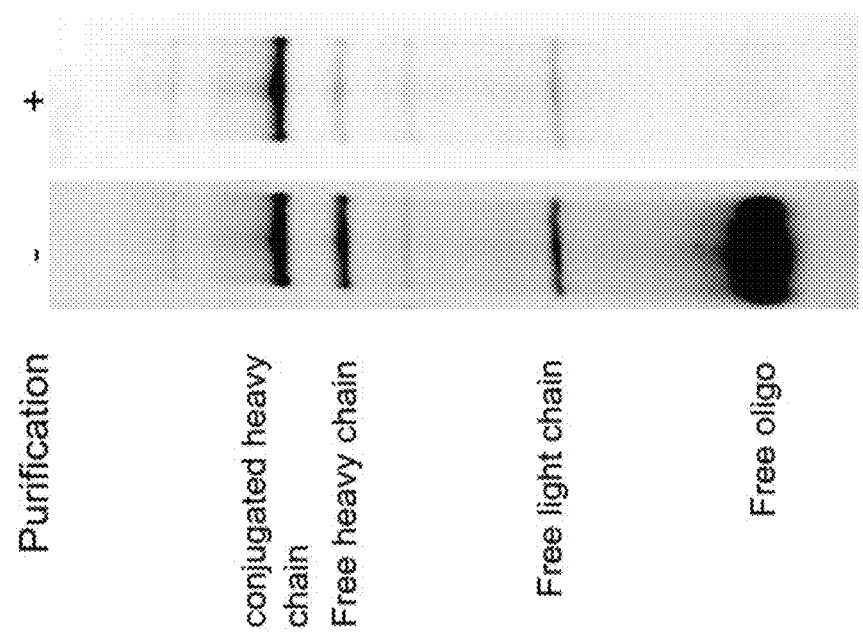
FIG. 4 is a photograph of an exemplary electrophoretic gel showing the purification of an antibody conjugated to an oligonucleotide that includes an antibody identifier sequence. The left panel shows the conjugated antibody prior to purification, and the right panel shows the conjugated antibody after purification.

Twenty µl of 100 µM oligo (synthesized with a 5' amine group) in H₂O, 2.4 µl of 10× borate buffer saline (pH 8.4), and 4 µl of 25 mM MeTZ (methyl tetrazine)-PEG4-NHS in DMSO were mixed and incubated at room temperature overnight. The next day, 100 µg (100 µl) antibody buffer was exchanged to 1× borate buffer saline (pH 8.4) on a 7 kD Zeba™ column (Thermo Scientific). Then, 0.6 µl of 10 mM TCO-PEG4-NHS was added to each antibody (CD8, CD56, CD4, CD3, CD19 and CD14 antibodies) and incubated at room temperature for 2 hours. The activated oligonucleotide and the antibody were cleaned up on a 7 kD Zeba™ column to remove unlabeled small molecules. The oligonucleotide and antibody were mixed at a 2:1 molar ratio and incubated at room temperature overnight. Antibody-oligonucleiotide conjugate was purified from free antibody and oligonucleotide by high performance size exclusion chromatography (FIG. 4).

Figure 7:
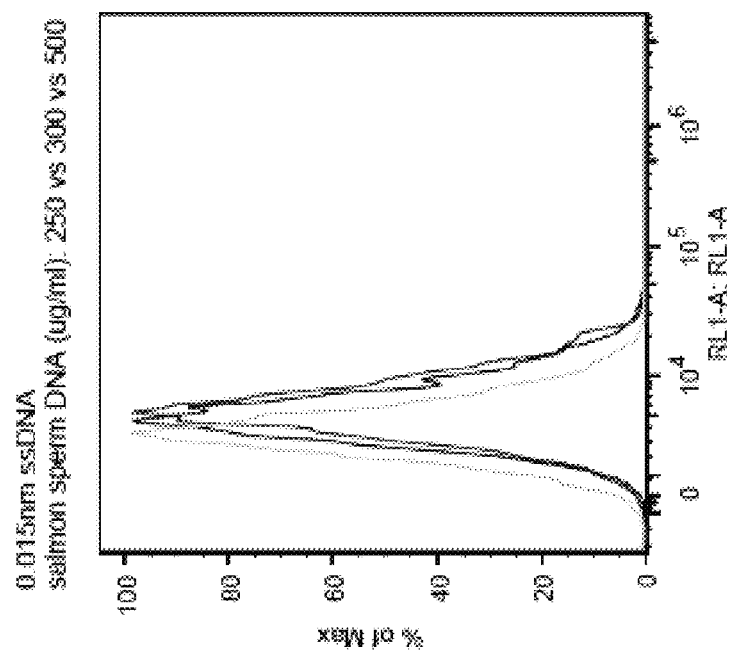
FIG. 7 is a graph showing that salmon sperm DNA reduces nonspecific background signal. In this experiment, lyophilized PBMCs (VERIcells) were stained with unconjugated oligonucleotides so that any signal observed is likely due to nonspecific staining. Background signal decreases as salmon sperm DNA blocking concentration increases from 250 μg/ml (medium gray curve) to 300 μg/ml (dark gray curve) to 500 μg/ml (light gray curve).

Then 0.5 µg of conjugated antibody was used to stain one million cells in 100 µl staining media (2% FBS, 1 mM EDTA, PBS) for 30 minutes at room temperature. Alternatively, to reduce background, the cells were incubated in blocking buffer containing: 1) about 50-300 µg/ml salmon sperm DNA or yeast tRNA; and 2) 2% FBS for about 30 minutes at 4° C., prior to contacting the cells with the conjugated antibody in 100 µl staining media (2% FBS, 1 mM EDTA, PBS) for about 15 to about 30 minutes at room temperature. As shown in FIG. 7, salmon sperm DNA helps reduce nonspecific background signal. Yeast tRNA blocking showed a similar effect (data not shown).

Cells were pelleted at 1000 g for 5 minutes and washed 3 times in staining media. After the last wash, cell pellets were resuspended in 100 µl PBS, and a small aliquot (1 µl) was added directly to the PCR reaction in order to amplify oligonucleotides into next generation sequencing libraries. Amplified libraries were size separated on a 1% agarose gel, the correctly sized library was excised out of the gel using a razor blade, and embedded DNA was extracted by the use of a gel extraction kit (Qiagen). The purified library was then analyzed by an Illumina sequencer.

The reads from a sequencing run contain an antibody identifier sequence (which is used to identify antibodies present), and unique molecular identifier sequences (UMI, which is used to eliminate PCR introduced duplicate molecules). A typical read is as follows:

(SEQ ID NO: 1)
GGTAGAAGTA*CTAGTACG*CTGTNTCTTATANACATCTCCGAGCCCACGA
G.

This read is 50 nucleotides, including 10 nucleotides of unique molecular identifier sequence (underlined), followed by 8 nucleotides of an antibody identifier sequence (italics), followed by 32 nucleotides of an adapter sequence.

Figure 5:
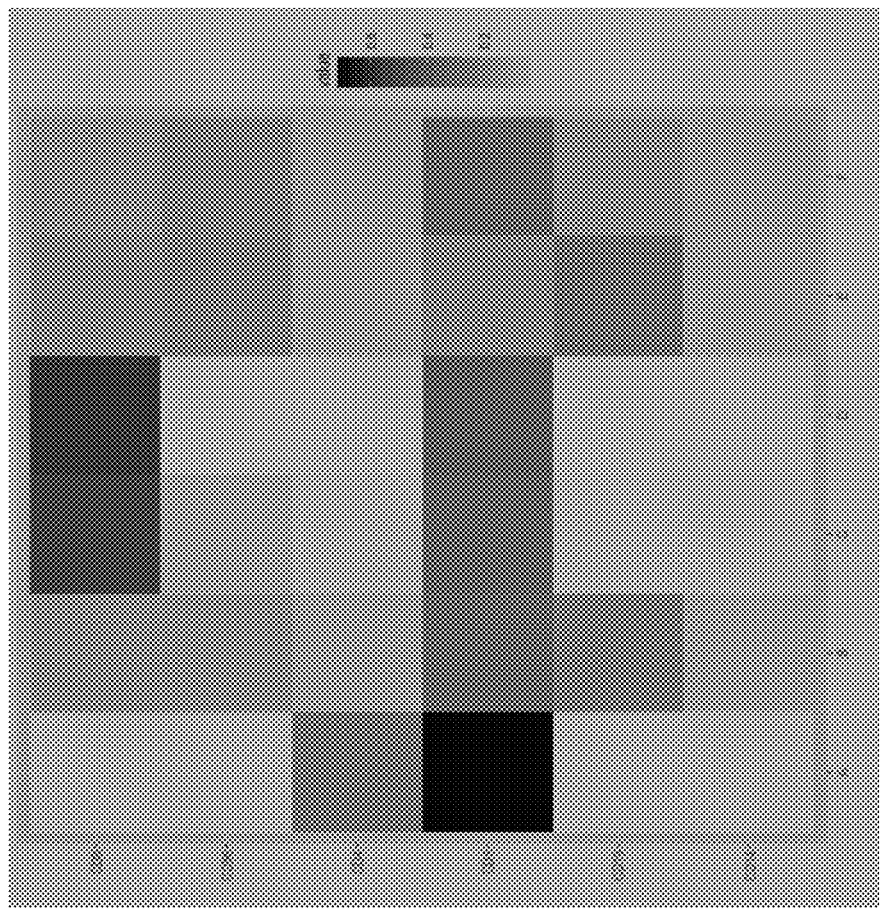
FIG. 5 is a graphical representation of cell-surface marker information for cell samples contacted with antibodies conjugated to an oligonucleotide that includes an antibody identifier sequence. The cell samples are indicated on the x axis, and the markers are indicated on the y axis. The shading of the squares indicates an increase in the level of expression of a particular parker. For example, Cell sample "A" contains increased amounts of CD3 and CD4 markers. Cell sample "D" shows increased amounts of CD3 and CD8 markers.

Six samples were analyzed. Reads were processed to de-duplicate (collapse reads containing identical UMI), and the counts of each antibody identifier sequence were tallied. The tally results of each sample identifies the antibodies present, and thus the identity of the cell population (FIG. 5). In this particular example, cell sample "A" contained high CD3 and CD4 marks, and cell sample "D" contained high CD3 and CD8 marks. Based on this surface marker information, it was deduced that cell sample "A" is a sample of helper T-cells, and cell sample "D" is a sample of cytotoxic T-cells, which was correct.

fier sequence and an antibody identifier sequence corresponding to the unique target antigen;
b) separating single cells of the population into individual compartments;
c) amplifying the unique molecular identifier sequences and antibody identifier sequences in each individual compartment; and
d) analyzing the amplified unique molecular identifier sequences and antibody identifier sequences to identify the expression profile of each single cell, wherein the unique molecular identifier sequences reduce bias in the analysis.

2. The method of claim 1, wherein the population of cells is fixed and permeabilized prior to contacting the population with the plurality of antibodies.

3. The method of claim 1, wherein each compartment further comprises an oligonucleotide comprising a unique cellular identifier sequence that corresponds to the single cell in each compartment.

4. The method of claim 3, wherein the unique molecular identifier sequence and antibody identifier sequence in each individual compartment are amplified using the oligonucleotide comprising the unique cellular identifier sequence that corresponds to the single cell in each individual compartment.

5. The method of claim 3, wherein the cellular identifier sequence corresponds to a well in a tissue culture plate.

6. The method of claim 1, wherein analyzing comprises sequencing the amplified unique molecular identifier sequences and antibody identifier sequences.

7. The method of claim 5, wherein the amplification products from the individual compartments are pooled prior to sequencing.

What is claimed is:

1. A method of identifying an expression profile in a single cell of a population of cells, comprising:
   a) contacting a population of cells with a plurality of antibodies under conditions that promote specific binding of the antibodies to target antigens of the cells, wherein each antibody in the plurality is capable of binding to a unique target antigen in one or more cells, wherein each antibody is conjugated to an oligonucleotide via thiol/maleimide conjugation, and wherein the oligonucleotide comprises a unique molecular identi- 8. The method of claim 7, wherein the pooled sequencing results are deconvoluted using the unique cellular identifier sequences to identify the expression profile of a single cell associated with each unique cellular identifier sequence.

9. The method of claim 1, wherein the individual compartments are wells of a tissue culture plate or microfluidic droplets.

10. A method of identifying an expression profile of a population of cells, comprising:
   a) contacting a population of cells with a plurality of antibodies under conditions that promote specific binding of the antibodies to the cells; wherein each antibody in the plurality is capable of binding to a unique target antigen in one or more cells, wherein each antibody is conjugated to an oligonucleotide via thiol/maleimide conjugation, and wherein the oligonucleotide comprises a unique molecular identifier sequence and an antibody identifier sequence corresponding to the unique target antigen;
b) amplifying the unique molecular identifier sequences and antibody identifier sequences; and
c) analyzing the amplified unique molecular identifier sequences and antibody identifier sequences to identify the expression profile of the population of cells, wherein the unique molecular identifier sequences reduce bias in the analysis.

11. The method of claim 10, wherein analyzing comprises sequencing the amplified unique molecular identifier sequences and antibody identifier sequences.

12. A method of identifying an expression profile of a population of cells, comprising:
a) lysing a population of cells;
b) labeling the cellular proteins in the cell lysate of step a) with an affinity label;
c) contacting the affinity labeled proteins with beads comprising an agent that binds the affinity label to generate protein-coated beads;
d) contacting the protein-coated beads with a plurality of antibodies under conditions that promote specific binding of the antibodies to the protein-coated beads; wherein each antibody in the plurality binds to a unique target protein, wherein each antibody is conjugated to an oligonucleotide, and wherein the oligonucleotide comprises a unique molecular identifier sequence and an antibody identifier sequence corresponding to the unique target protein;
e) amplifying the unique molecular identifier sequences and antibody identifier sequences; and
f) analyzing the amplified unique molecular identifier sequences and antibody identifier sequences to identify the expression profile of the population of cells, wherein the unique molecular identifier sequences reduce bias in the analysis.

13. The method of claim 12, wherein single cells of the population are separated into individual compartments prior to the lysing of the cells.

14. The method of claim 13, wherein each compartment further comprises an oligonucleotide comprising a unique cellular identifier sequence that corresponds to the single cell in each compartment.

15. The method of claim 14, wherein the antibody identifier sequence in each individual compartment is amplified using the oligonucleotide comprising the unique cellular identifier sequence that corresponds to the single cell in each individual compartment.

16. The method of claim 14, wherein the cellular identifier sequence corresponds to a well in a tissue culture plate.

17. The method of claim 12, wherein analyzing comprises sequencing the amplified unique molecular identifier sequence and antibody identifier sequences.

18. The method of claim 17, wherein the amplification products from the individual compartments are pooled prior to sequencing.

19. The method of claim 18, wherein the pooled sequencing results are deconvoluted using the unique cellular identifier sequences to identify the expression profile of a single cell associated with each unique cellular identifier sequence.

20. The method of claim 13, wherein the individual compartments are wells of a tissue culture plate or microfluidic droplets.

* * * * *